United States Patent
Cho et al.

(12)

(10) Patent No.: US 11,795,227 B2
(45) Date of Patent: *Oct. 24, 2023

(54) IMMUNOMODULATION AND ANTI-TUMOR-RELATED NANOBODY AND NUCLEIC ACID ENCODING SEQUENCE THEREOF, AND USES OF THE SAME

(71) Applicant: Shine-On Biomedical Co., Ltd., Taichung (TW)

(72) Inventors: Der-Yang Cho, Taichung (TW); Shao-Chih Chiu, Taichung (TW); Shi-Wei Huang, Taichung (TW); Chih-Ming Pan, Taichung (TW); Mei-Chih Chen, Taichung (TW); Yu-Chuan Lin, Taichung (TW); Yeh Chen, Taichung (TW)

(73) Assignee: SHINE-ON BIOMEDICAL CO., LTD., Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/699,879

(22) Filed: Mar. 21, 2022

(65) Prior Publication Data

US 2022/0306748 A1  Sep. 29, 2022

Related U.S. Application Data

(60) Provisional application No. 63/165,191, filed on Mar. 24, 2021, provisional application No. 63/165,266, filed on Mar. 24, 2021, provisional application No. 63/165,274, filed on Mar. 24, 2021.

(51) Int. Cl.
  *C07K 16/28* (2006.01)
  *A61P 35/00* (2006.01)
  *A61K 39/00* (2006.01)

(52) U.S. Cl.
  CPC .......... *C07K 16/2833* (2013.01); *A61P 35/00* (2018.01); *C07K 16/2809* (2013.01); *C07K 16/2827* (2013.01); *A61K 2039/505* (2013.01); *C07K 2317/31* (2013.01); *C07K 2317/52* (2013.01); *C07K 2317/524* (2013.01); *C07K 2317/526* (2013.01); *C07K 2317/569* (2013.01); *C07K 2317/73* (2013.01); *C07K 2317/74* (2013.01)

(58) Field of Classification Search
  CPC ............ C07K 16/2833; C07K 16/2809; C07K 16/2827; C07K 2317/52; A61P 35/00; A61K 2039/505
  See application file for complete search history.

(56) References Cited

PUBLICATIONS

Almagro JC, Fransson J. Humanization of antibodies. Front Biosci. Jan. 1, 2008;13:1619-33. (Year: 2008).*
Edwards et al. The remarkable flexibility of the human antibody repertoire;isolation of over one thousand different antibodies to a single protein, BLyS. J Mol Biol Nov. 14, 2003;334(1):103-18. (Year: 2003).*
Muyldermans S. Nanobodies: natural single-domain antibodies. Annu Rev Biochem. 2013;82:775-97. doi: 10.1146/annurev-biochem-063011-092449. Epub Mar. 13, 2013. (Year: 2013).*
Kussie et al. A single engineered amino acid substitution changes antibody fine specificity.J Immunol. Jan. 1, 1994;152(1):146-52. (Year: 1994).*
Chen et al. Enhancement and destruction of antibody function by somatic mutation: unequal occurrence is controlled by V gene combinatorial associations.EMBO J. Jun. 15, 1995; 14(12): 2784-94. (Year: 1995).*
Koenig et al. Mutational landscape of antibody variable domains reveals a switch modulating the interdomain conformational dynamics and antigen binding.PNAS Jan. 24, 2017 114(4)E486-E495;firstpublished Jan. 5, 2017. (Year: 2017).*
Krijgsman D, Roelands J, Hendrickx W, Bedognetti D, Kuppen PJK. HLA-G: A New Immune Checkpoint in Cancer? Int J Mol Sci. Jun. 25, 2020;21(12):4528. (Year: 2020).*
Pishvaian M et al. Phase 1 Dose Escalation Study of MEDI-565, a Bispecific T-Cell Engager that Targets Human Carcinoembryonic Antigen, in Patients With Advanced Gastrointestinal Adenocarcinomas. Clin Colorectal Cancer. Dec. 2016; 15(4):345-351. (Year: 2016).*

* cited by examiner

*Primary Examiner* — Aurora M Fontainhas
*Assistant Examiner* — Jennifer A Benavides
(74) *Attorney, Agent, or Firm* — WPAT, PC

(57) ABSTRACT

The present disclosure provides an immunomodulation and anti-tumor-related nanobody that specifically binds to a human leukocyte antigen-G, a programmed cell death ligand 1, and CD3 ε. The present disclosure also provides the nucleic acid sequence of the immunomodulation and anti-tumor-related nanobody, and use of the immunomodulation and anti-tumor-related nanobody for treating cancer and immune-related disorders.

13 Claims, 12 Drawing Sheets
(2 of 12 Drawing Sheet(s) Filed in Color)
Specification includes a Sequence Listing.

SEQUENCE LISTING

<160> NUMBER OF SEQ ID NOS: 12

<210> SEQ ID NO 1
<211> LENGTH: 128
<212> TYPE: PRT
<213> ORGANISM: Artificial Sequence
<220> FEATURE:
<223> OTHER INFORMATION: anti-HLA-G nanobody

<400> SEQUENCE: 1

His Val Gln Leu Val Glu Ser Gly Gly Gly Ser Val Gln Ala Gly Gly
1               5                   10                  15

Ser Leu Lys Leu Ser Cys Val Thr Ser Ala Tyr Thr Phe Ser Ala Ser
            20                  25                  30

Gly Asn Cys Met Gly Trp Leu Arg Gln Ala Pro Gly Lys Gly Arg Glu
            35                  40                  45

Gly Ile Ala Ala Thr Tyr Thr Arg Ser Ala Lys Thr Tyr Tyr Ala Asp
        50                  55                  60

Ser Val Lys Gly Arg Phe Thr Ile Ser Gln Asp Asn Ala Lys Asn Thr
65                  70                  75                  80

Val Tyr Leu Gln Met Asn Gly Leu Lys Pro Glu Asp Thr Ala Thr Tyr
                85                  90                  95

Tyr Cys Ala Val Ala Arg Cys Ala Gly Arg Pro Asp Arg Ser Thr Leu
                100                 105                 110

Thr Ser Phe Ala Trp Trp Gly Gln Gly Thr Gln Val Thr Val Ser Ser
            115                 120                 125

<210> SEQ ID NO 2
<211> LENGTH: 121
<212> TYPE: PRT
<213> ORGANISM: Artificial Sequence
<220> FEATURE:
<223> OTHER INFORMATION: anti-PD-L1 nanobody

<400> SEQUENCE: 2

His Val Gln Leu Val Glu Ser Gly Gly Gly Leu Val Gln Pro Gly Gly
1               5                   10                  15

Ser Leu Arg Ile Ser Cys Ala Ala Ser Gly Phe Thr Phe Ser Ser Arg
            20                  25                  30

Ala Met Ser Trp Val Arg Gln Ala Pro Gly Lys Gly Leu Glu Trp Val
            35                  40                  45

Ser Thr Ile Asn Ser Asp Gly Ser Asn Thr Tyr Tyr Ser Asp Ser Val
        50                  55                  60

Lys Asp Arg Phe Thr Ile Ser Arg Asp Asn Ala Ile Asn Thr Leu Tyr
65                  70                  75                  80

Leu Gln Leu Asn Ser Leu Lys Thr Glu Asp Thr Ala Met Tyr Tyr Cys
                85                  90                  95

Ser Arg Cys Pro Asp Ile Tyr Cys Gly Gly Gln Tyr Thr Tyr Arg Gly
                100                 105                 110

Gln Gly Thr Gln Val Thr Val Ser Ser
        115                 120

<210> SEQ ID NO 3
<211> LENGTH: 128
<212> TYPE: PRT
<213> ORGANISM: Artificial Sequence
<220> FEATURE:
<223> OTHER INFORMATION: anti-CD3 epsilon nanobody

<400> SEQUENCE: 3

His Val Gln Leu Val Glu Ser Gly Gly Gly Ser Val Gln Ala Gly Gly
1               5                   10                  15

Ser Leu Arg Leu Ser Cys Thr Val Ser Gly Val Ile Phe Lys Asn Glu
            20                  25                  30

Tyr Met Gly Trp Phe Arg Gln Ala Pro Gly Lys Glu Arg Glu Gly Val
            35                  40                  45

Ala Ala Ala Ser Pro Gly Gly Thr Ile Thr Tyr Tyr Gly Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Arg Leu Lys Pro Glu Asp Thr Ala Met Tyr Tyr Cys
                85                  90                  95

Ala Leu Asp Pro Ser Thr Thr Ser Trp Ser Ile Ile Arg His Gly Pro
            100                 105                 110

Ser Leu Trp Arg Tyr Ser Gly Arg Gly Thr Gln Val Thr Val Ser Ser
        115                 120                 125

<210> SEQ ID NO 4
<211> LENGTH: 384
<212> TYPE: DNA
<213> ORGANISM: Artificial Sequence
<220> FEATURE:
<223> OTHER INFORMATION: anti-HLA-G nanobody

<400> SEQUENCE: 4
cacgttcagt tggtagagtc cggcggagga tcagtccagg ccggggggatc cctcaaactg     60 tcttgtgtga ccagtgcata cactttctca gcttctggaa actgcatggg atggttgagg    120
caggctcccg gtaaaggcag ggaggggatc gccgccacct atacccgcag cgcaaagaca    180
tactatgccg actccgtgaa aggtaggttc accatctccc aggacaacgc caaaaacact    240
gtttatcttc agatgaacgg tcttaagccc gaggacacag ccacctacta ttgtgccgtg    300
gcacgatgcg ctggcaggcc agaccgcagt accctgacca gcttcgcttg gtggggccaa    360
ggcacacagg tcaccgtcag ctcc                                           384

<210> SEQ ID NO 5
<211> LENGTH: 363
<212> TYPE: DNA
<213> ORGANISM: Artificial Sequence
<220> FEATURE:
<223> OTHER INFORMATION: anti-PD-L1 nanobody

<400> SEQUENCE: 5
catgtgcaac tggtagaatc aggagggggc ctggtccagc caggcggttc cctcaggatc     60
agttgtgccg catccgggtt tactttcagc tccagggcca tgtcctgggt gcgccaggct    120
cctggcaaag gtctggaatg ggtctccaca attaatagcg atggcagcaa tacctactat    180
agcgactcag tgaaggatag attcactatc tcacgggata cgccattaa cactctgtac    240 ctgcagctca acagcctgaa gaccgaagac acagccatgt actactgttc acggtgccca    300
gacatctact gcggcgggca gtacacctac cgcggacagg gcacacaggt gacagtgtct    360
tcc                                                                  363

<210> SEQ ID NO 6
<211> LENGTH: 384
<212> TYPE: DNA
<213> ORGANISM: Artificial Sequence
<220> FEATURE:
<223> OTHER INFORMATION: anti-CD3 epsilon nanobody

<400> SEQUENCE: 6
catgtgcagc tggtggagtc tgggggaggc tcggtgcagg ctgggggggtc tctgagactc     60 tcctgtacag tgtctggagt catctttaag aacgagtaca tgggctggtt ccgccaggcc    120
ccagggaagg agcgcgaggg ggtcgcagca gcttcgcctg gtggaacgat tacatactat    180
ggggactccg tgaagggccg attcaccatc tcccgagaca atgccaagaa cacggtgtat    240

```
ctgcaaatga accgcctgaa acctgaggac actgccatgt actactgtgc gttggatccc    300
tcgactacgt catggtctat catccgccac ggtccatcgc tttggcgtta tagcggccgg    360
gggacccagg tcaccgtctc ctca                                           384
```

```
<210> SEQ ID NO 7
<211> LENGTH: 19
<212> TYPE: PRT
<213> ORGANISM: Artificial Sequence
<220> FEATURE:
<223> OTHER INFORMATION: signal peptide

<400> SEQUENCE: 7
```

Met Gly Trp Ser Cys Ile Ile Leu Phe Leu Val Ala Thr Ala Thr Gly
1               5                   10                  15

Val His Ser

```
<210> SEQ ID NO 8
<211> LENGTH: 57
<212> TYPE: DNA
<213> ORGANISM: Artificial Sequence
<220> FEATURE:
<223> OTHER INFORMATION: signal peptide

<400> SEQUENCE: 8
```
atgggatgga gctgtattat tctcttcctt gtcgctacag caactggggt tcacagc       57

```
<210> SEQ ID NO 9
<211> LENGTH: 15
<212> TYPE: PRT
<213> ORGANISM: Artificial Sequence
<220> FEATURE:
<223> OTHER INFORMATION: flexible linker

<400> SEQUENCE: 9
```

Gly Gly Gly Gly Ser Gly Gly Gly Ser Gly Gly Gly Gly Ser
1               5                   10                  15

```
<210> SEQ ID NO 10
<211> LENGTH: 45
<212> TYPE: DNA
<213> ORGANISM: Artificial Sequence
<220> FEATURE:
<223> OTHER INFORMATION: flexible linker

<400> SEQUENCE: 10
```
ggaggaggag gctccggagg aggcggaagc ggaggaggag gaagc                    45

```
<210> SEQ ID NO 11
<211> LENGTH: 232
<212> TYPE: PRT
<213> ORGANISM: Artificial Sequence
<220> FEATURE:
<223> OTHER INFORMATION: human IgG1 Fc-domain

<400> SEQUENCE: 11
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Tyr
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 12
<211> LENGTH: 699
<212> TYPE: DNA
<213> ORGANISM: Artificial Sequence
<220> FEATURE:
<223> OTHER INFORMATION: human IgG1 Fc-domain

<400> SEQUENCE: 12
gaaccaaaga gttgcgacaa gactcatacc tgcccaccat gtccagctcc tgaactgctg      60
gggggaccca gtgtgttcct gttccccct aagcccaagg ataccctat gattagcaga      120 acgcctgagg ttacttgtgt ggttgtcgat gtgagccatg aagatccaga ggtgaagttc      180
aactggtatt acgacggggt ggaggtgcat aacgctaaga ccaaaccaag ggaggaacaa      240
tataacagca cctatagagt cgtgtccgtc ctgaccgtgc tgcaccaaga ctggctcaat      300
ggtaaagaat acaagtgcaa ggtttccaac aaggcactgc ctgctccgat gaaaaaaacc      360
attagtaaag caaggggca acctcgagaa ccacaggtgt ataccctccc acctagtcgc      420
gaggagatga caaagaacca ggtatccctc acctgtcttg tgaagggggtt ctacccaagt      480 gacatcgccg ttgaatggga gtctaacggt cagccagaaa acaactacaa gaccactccg      540
cctgtcctgg actcagacgg gagcttcttc ctgtacagca gttgaccgt ggataagagt      600 agatggcagc aggggaatgt gttcagctgc agcgttatgc acgaggccct gcacaatcac      660
tacacccaga atccctcag cctgtcacca gggaagtaa                            699

IMMUNOMODULATION AND ANTI-TUMOR-RELATED NANOBODY AND NUCLEIC ACID ENCODING SEQUENCE THEREOF, AND USES OF THE SAME

CROSS-REFERENCE TO RELATED APPLICATION

This application claims priorities of Provisional Application No. 63/165,191, 63/165,266, and 63/165,274, filed on Mar. 24, 2021, the content of which is incorporated herein in its entirety by reference.

BACKGROUND OF THE INVENTION

1. Field of the Invention

The present invention relates to an immunomodulation and anti-tumor-related nanobody and nucleic acid encoding sequences thereof, and uses of the same.

2. The Prior Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for consecutive years.

Conventional cancer treatments include surgery, radiation therapy, chemotherapy, and target therapy. Cancer immunotherapy is another method for treating cancer except the above methods. The immune system of the patient is activated in the cancer immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors. However, the current tumor treatments still have the problems of ineffectiveness and strong side effects, and even lead to other immune-related disorders.

Human leukocyte antigen-G (HLA-G) has been found to be highly expressed on a variety of solid tumors, and has the property of suppressing immune cells. Therefore, researchers have been committed to developing HLA-G as target molecules for tumor identification and to find out whether these target molecules have the potential to become anti-cancer drugs.

Programmed cell death ligand 1 (PD-L1) has been found to be expressed on the cell surface of a variety of solid tumors. Therefore, researchers have been committed to developing PD-L1 as target molecules for tumor identification and to find out whether these target molecules have the potential to become anticancer drugs.

CD3ε (CD3 epsilon), a transmembrane protein found on T cells, has been found to be associated with tumors and regulation of immune function. Therefore, researchers have been committed to developing CD3ε as target molecules for tumor identification and regulation of immune function and to find out whether these target molecules have the potential to become anticancer drugs or immunoregulatory drugs.

In order to solve the above-mentioned problems, those skilled in the art urgently need to develop a novel and effective medicament for treating cancer and immune-related disorders, immunoregulation and activating immune cells for the benefit of a large group of people in need thereof.

SUMMARY OF THE INVENTION

A primary objective of the present invention is to provide an immunomodulation and anti-tumor-related nanobody that specifically binds to a human leukocyte antigen-G (HLA-G), programmed cell death ligand 1 (PD-L1) and CD3 ε (CD3 epsilon), comprising a combination of amino acid sequences including SEQ ID NO:1, SEQ ID NO:2, and SEQ ID NO:3.

According to an embodiment of the present invention, the combination of amino acid sequences is an amino acid sequence of a heavy chain variable domain (VHH) of the immunomodulation and anti-tumor-related nanobody.

According to an embodiment of the present invention, the immunomodulation and anti-tumor-related nanobody further comprises a fragment crystallizable region (Fc region).

According to an embodiment of the present invention, the immunomodulation and anti-tumor-related nanobody is conjugated with a second antibody to form a triple specific T-cell engager (TriTE).

According to an embodiment of the present invention, the immunomodulation and anti-tumor-related nanobody activates and/or aggregates CD3-positive cells.

According to an embodiment of the present invention, the immunomodulation and anti-tumor-related nanobody has effect on killing tumor cells.

According to an embodiment of the present invention, the tumor cells are selected from the group consisting of: lung adenocarcinoma cells, breast cancer cells, glioblastoma cells, ovarian carcinoma cells, oral cancer cells, and a combination thereof.

Another objective of the present invention is to provide an isolated nucleic acid encoding the above mentioned immunomodulation and anti-tumor-related nanobod, wherein the isolated nucleic acid comprises a combination of nucleotide sequences including SEQ ID NO:4, SEQ ID NO:5, and SEQ ID NO:6.

Another objective of the present invention is to provide a pharmaceutical composition, comprising the above mentioned the immunomodulation and anti-tumor-related nanobody and a pharmaceutically acceptable carrier.

Another objective of the present invention is to provide a method for treating cancer and immune-related disorders, comprising administering to a subject in need thereof the above mentioned pharmaceutical composition.

According to an embodiment of the present invention, the cancer is selected from the group consisting of: lung adenocarcinoma, breast cancer, glioblastoma, ovarian carcinoma, oral cancer, and a combination thereof.

In summary, the immunomodulation and anti-tumor-related nanobody of the present invention has the following effect. The immunomodulation and anti-tumor-related nanobody effectively binds to HLA-G, PD-L1 and CD3 ε, respectively, by surface plasmon resonance binding assay (SPR binding assay), promotes T cell proliferation and activation by T cell (i.e., peripheral blood mononuclear cell (PBMC)) proliferation and activation assay, enhances CD3 positive T cell proliferation in PBMCs, binds to tumor cells and kills tumor cells by immunocytochemistry (ICC) staining, enhances cytokine secretion in tumor cells by enzyme linked immunosorbent assay (ELISA), inhibits cancer cell growth by animal experiments, thereby achieving the effect of treating cancer and immune-related disorders. In particular, compared with the conventional antibodies, which have the disadvantages of low yield and poor effect, the gene must be transfected into cells by a vector to express the antibody function, the immunomodulation and anti-tumor-related nanobody of the present invention can be prepared in vitro on a large scale, and directly administered to the individual in need for treatment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included here to further demonstrate some aspects of the present invention, which can be better understood by reference to one or more of these drawings, in combination with the detailed description of the embodiments presented herein.

FIG. 7B shows the result regarding bioluminescence and tumor weight for Nb-TriTE; FIG. 7C shows the result regarding survival rate after PBMC and Nb-TriTE infusion; PBMC represents peripheral blood mononuclear cell; A549 represents human lung adenocarcinoma cell line; TriTE represents Nb-TriTE.

DETAILED DESCRIPTION OF THE PREFERRED EMBODIMENT

Figure 1A:
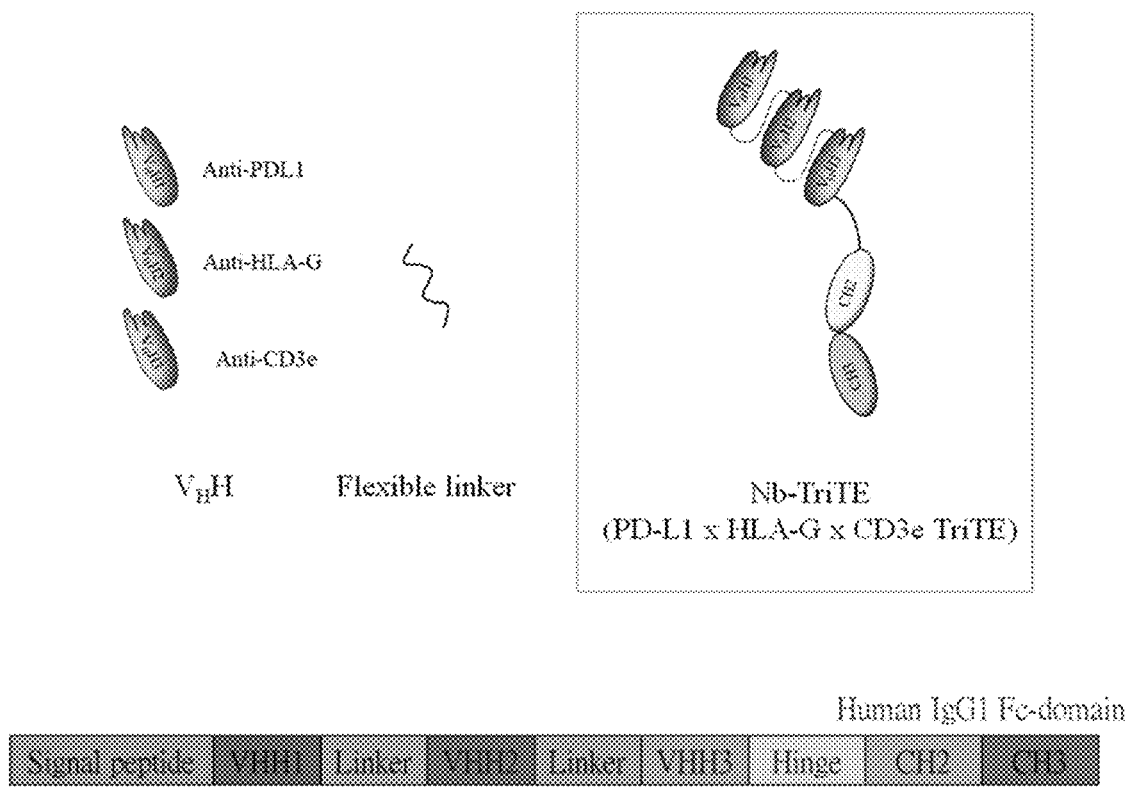
FIG. 1A shows the structure and composition of the immunomodulation and anti-tumor-related nanobody (i.e., PD-L1×HLA-G×CD3ε nanobody-based triple specific T-cell engager (PD-L1×HLA-G×CD3ε nanobody-based TriTE), hereinafter referred to as Nb-TriTE), wherein Anti-HLA-G represents anti-human leukocyte antigen-G (HLA-G) nanobody, the amino acid sequence of the anti-HLA-G nanobody is SEQ ID NO:1, and the nucleotide sequence encoding the amino acid sequence of the anti-HLA-G nanobody is SEQ ID NO:4; Anti-PDL1 represents anti-programmed cell death ligand 1 (PD-L1) nanobody, the amino acid sequence of the anti-PD-L1 nanobody is SEQ ID NO:2, and the nucleotide sequence encoding the amino acid sequence of the anti-PD-L1 nanobody is SEQ ID NO:5; Anti-CD3e represents anti-CD3ε nanobody, the amino acid sequence of the anti-CD3ε nanobody is SEQ ID NO:3, and the nucleotide sequence encoding the amino acid sequence of the anti-CD3ε nanobody is SEQ ID NO:6; the amino acid sequence of the signal peptide is SEQ ID NO:7, and the nucleotide sequence encoding the amino acid sequence of the signal peptide is SEQ ID NO:8; VHH1 represents heavy chain variable domain 1 (i.e., anti-PD-L1 nanobody); Flexible linker represents linker, the amino acid sequence of the flexible linker is SEQ ID NO:9, and the nucleotide sequence encoding the amino acid sequence of the flexible linker is SEQ ID NO:10; VHH2 represents heavy chain variable domain 2 (i.e., anti-HLA-G nanobody); VHH3 represents heavy chain variable domain 3 (i.e., anti-CD3ε nanobody); CH2 and CH3 represent human fragment crystallizable region (Fc region), that is, human IgG1 Fc-domain, the amino acid sequence of the human IgG1 Fc-domain is SEQ ID NO:11, and the nucleotide sequence encoding the amino acid sequence of the human IgG1 Fc-domain is SEQ ID NO:12.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the terms "immunomodulation and anti-tumor-related nanobody", "PD-L1×HLA-G×CD3ε nanobody-based triple specific T-cell engager (PD-L1×HLA-G×CD3ε nanobody-based TriTE)", "Nb-TriTE", and "$V_HH$ nanobody" can be used interchangeably.

As used herein, the terms "CD3e", "CD3 ε" and "CD3 epsilon" can be used interchangeably.

As used herein, the term "second antibody" refers to the antibody conjugated with the nanobody to form a triple specific T-cell engager (TriTE). Preferably, the second antibody includes, but is not limited to, anti-CD3ε antibody, anti-CD3 antibody, anti-human leukocyte antigen-G (HLA-G) antibody, anti-programmed cell death ligand 2 (PD-L2) antibody, anti-T-cell immunoglobulin domain and mucin domain 3 (Tim3) antibody, anti-epidermal growth factor receptor (EGFR) antibody, anti-EGFRvIII antibody, anti-human epidermal growth factor receptor 2 (Her2) antibody, anti-B-cell maturation antigen (BCMA) antibody, anti-CD19 antibody, anti-CD20 antibody, anti-CD34 antibody, anti-CD16 antibody, Fc, anti-epithelial cell adhesion molecule (EpCAM) antibody, anti-mesothelin antibody, anti-New York esophageal squamous cell carcinoma-1 (NY-ESO-1) antibody, anti-glycoprotein 100 (gp100) antibody, and anti-Muc antibody.

As used herein, the term "treating" or "treatment" refers to alleviating, reducing, ameliorating, relieving or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, and intralesional injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

As used herein, the term "nucleic acid", "nucleic acid sequence" or "nucleic acid fragment" refers to a sequence of deoxyribonucleotides or ribonucleotides in single- or double-stranded forms, and comprises known naturally occurring nucleotides or artificially chemical mimics. As used herein, the term "nucleic acid" is used interchangeably with the terms "gene", "cDNA", "mRNA", "oligonucleotide" and "polynucleotide".

Example 1

Preparation of Immunomodulation and Anti-Tumor-Related Nanobody

In this example, the preparation process of the immunomodulation and anti-tumor-related nanobody (i.e., PD-L1×HLA-G×CD3ε nanobody-based triple specific T-cell engager (PD-L1×HLA-G×CD3ε nanobody-based TriTE), hereinafter referred to as Nb-TriTE) is as follows. The Nb-TriTE gene was constructed in expression vector pcDNA3.4 (Amp resistance); The plasmid was identified by restriction enzyme digestion and sequenced verification. The plasmid was transduced into 293F cells by lipofectamine 3000, and incubated for 3 days at 37° C. with 8% $CO_2$. The supernatant was harvested by centrifugation. Supernatant was combined with protein A beads (1 mL) by flow-through. The protein A beads were washed and eluted with buffers containing suitable gradient imidazole (10 mM, 20 mM, 50 mM, 100 mM, 250 mM and 500 mM). Elution fraction was analyzed by SDS-PAGE, and the subsequent purification scheme was determined according to the purity and yield of the protein (ion exchange chromatography or gel filtration chromatography). The protein that meets the requirements was separated and purified by gel filtration chromatography, and buffer was replaced with PBS buffer. The protein component was analyzed by SDS-PAGE, the components were merged and concentrated that meet the requirements, filtered with 0.22 m filter and aliquot. The protein was stored at −20° C. or lower.

The structure and composition of the Nb-TriTE is shown in FIG. 1A, wherein Anti-HLA-G represents anti-human leukocyte antigen-G (HLA-G) nanobody, the amino acid sequence of the anti-HLA-G nanobody is SEQ ID NO:1, and the nucleotide sequence encoding the amino acid sequence of the anti-HLA-G nanobody is SEQ ID NO:4; Anti-PDL1 represents anti-programmed cell death ligand 1 (PD-L1) nanobody, the amino acid sequence of the anti-PD-L1 nanobody is SEQ ID NO:2, and the nucleotide sequence encoding the amino acid sequence of the anti-PD-L1 nanobody is SEQ ID NO:5; Anti-CD3e represents anti-CD3ε nanobody, the amino acid sequence of the anti-CD3ε nanobody is SEQ ID NO:3, and the nucleotide sequence encoding the amino acid sequence of the anti-CD3ε nanobody is SEQ ID NO:6; the amino acid sequence of the signal peptide is SEQ ID NO:7, and the nucleotide sequence encoding the amino acid sequence of the signal peptide is SEQ ID NO:8; VHH1 represents heavy chain variable domain 1 (i.e., anti-PD-L1 nanobody); Flexible linker represents linker, the amino acid sequence of the flexible linker is SEQ ID NO:9, and the nucleotide sequence encoding the amino acid sequence of the flexible linker is SEQ ID NO:10; VHH2 represents heavy chain variable domain 2 (i.e., anti-HLA-G nanobody); VHH3 represents heavy chain variable domain 3 (i.e., anti-CD3ε nanobody); CH2 and CH3 represent human fragment crystallizable region (Fc region), that is, human IgG1 Fc-domain, the amino acid sequence of the human IgG1 Fc-domain is SEQ ID NO:11, and the nucleotide sequence encoding the amino acid sequence of the human IgG1 Fc-domain is SEQ ID NO:12.

Figure 1B:
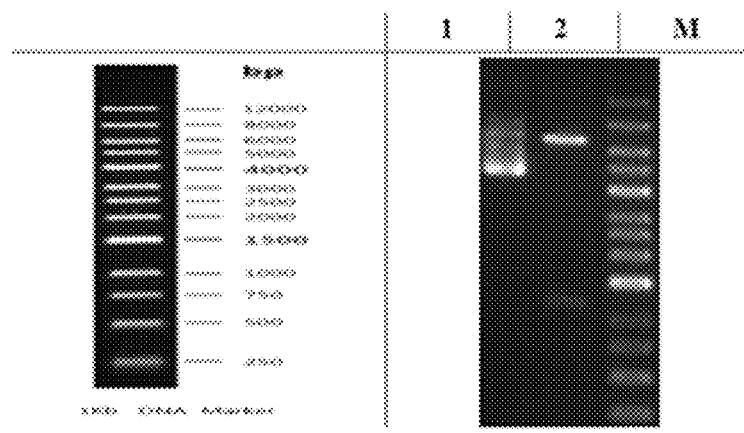
FIG. 1B shows restriction enzyme digestion result of the Nb-TriTE, wherein lane 1 represents plasmid, lane 2 represents plasmid digested with XbaI-BamHI, and lane M represents DNA marker.

Restriction enzyme digestion result of the Nb-TriTE is shown in FIG. 1B, wherein lane 1 represents plasmid, lane 2 represents plasmid digested with XbaI-BamHI, and lane M represents DNA marker.

Figure 1C:
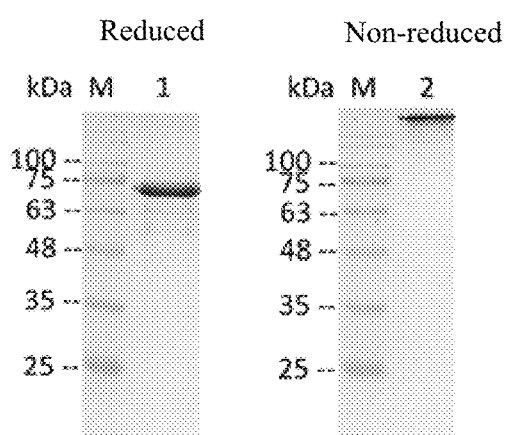
FIG. 1C shows the result of gel electrophoresis analysis of the purified Nb-TriTE.

The result of gel electrophoresis analysis of the purified Nb-TriTE is shown in FIG. 1C.

Example 2

Surface Plasmon Resonance Binding Assay (SPR Binding Assay) Result of Nb-TriTE

In this example, the procedures of the surface plasmon resonance binding assay (SPR binding assay) of the Nb-TriTE are as follows. The CM5 or NTA chip, research grade would be performed for SPR analysis by BIAcore T200 (Biacore-GE Healthcare, Piscataway, N.J.). Briefly, protein (PD-L1, HLA-G or CD3 recombinant protein) sample was diluted in the 10 mM buffer solutions (pH 4.0, 5.5 or 6.0) at the concentration range of 20 µg/mL to give maximum surface retention for immobilization on the chip, following the preparation process and choosing the condition of higher surface concentration of ligands (with 25, 12.5, 6.25, 3.125, 1.5625 and 0.78125 nM) on the chip. Then the regeneration scouting and surface performance test, following regeneration scouting and surface performance test and then regeneration method was selected to run the experiment. And then binding analysis and direct binding were selected to investigate protein binding. the kinetic analysis would be selected and choose mass transfer was chosen to run kinetic assay accompany with binding experiment. Data analysis and kinetic constants were determined.

Figure 2A:
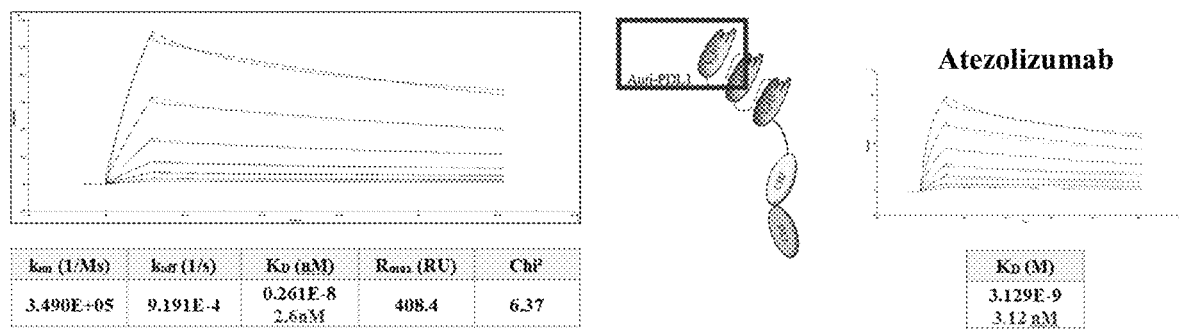
FIG. 2A shows SPR kinetics assay of PD-L1 binding to Nb-TriTE, wherein the ligand is PD-L1; analyte concentrations are 100, 50, 25, 12.5, 6.25, 3.125, 1.5625, 0.78125 nM; flow rate is 30 µL/min; association time is 120 seconds; dissociation time is 900 seconds; Atezolizumab is a monoclonal antibody medication used to treat urothelial carcinoma, non-small cell lung cancer (NSCLC), triple-negative breast cancer (TNBC), small cell lung cancer (SCLC), and hepatocellular carcinoma (HCC), and it is a fully humanized, engineered monoclonal antibody of IgG1 isotype against the protein programmed cell death-ligand 1 (PD-L1); Anti-PDL1 represents anti-PD-L1 nanobody.
Figure 2B:
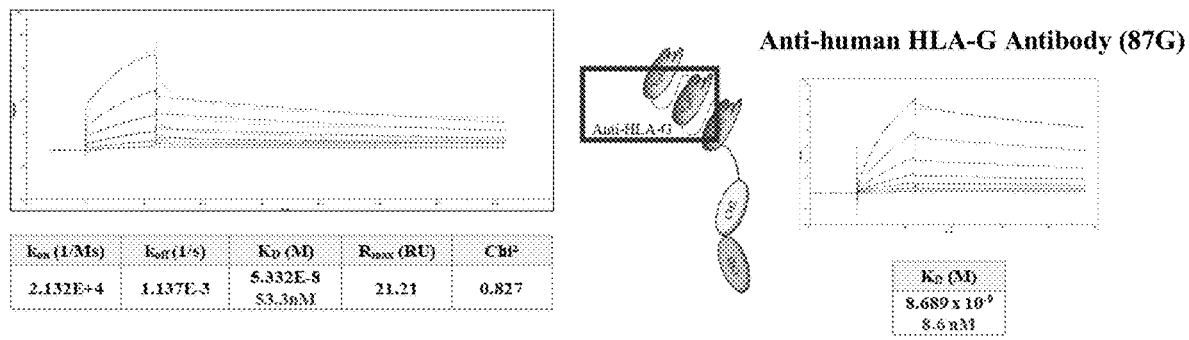
FIG. 2B shows SPR kinetics assay of HLA-G binding to Nb-TriTE, wherein the ligand is HLA-G; analyte concentrations are 305, 152.5, 76.25, 38.125, 19.0625 nM; flow rate is 30 µL/min; association time is 180 seconds; dissociation time is 360 seconds; Anti-HLA-G represents anti-HLA-G nanobody; Anti-CD3e represents anti-CD3ε nanobody; 87G represents commercial anti-HLA-G monoclonal antibody.
Figure 2C:
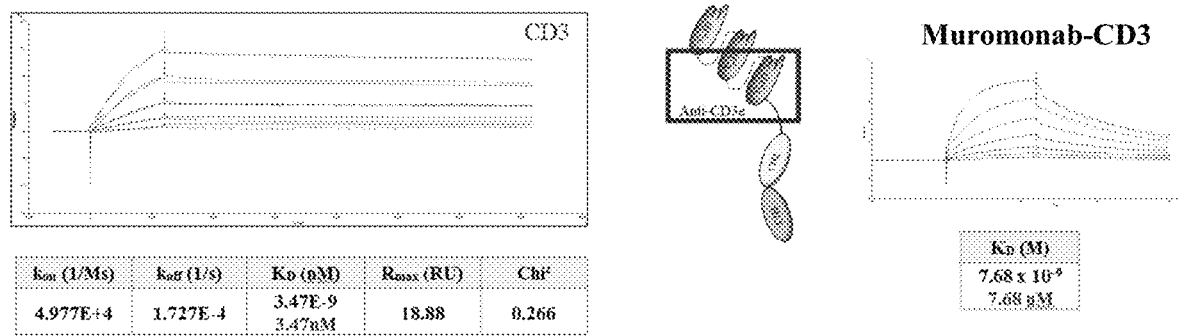
FIG. 2C shows SPR kinetics assay of CD3ε binding to Nb-TriTE, wherein the ligand is CD3ε; analyte concentrations are 28.125, 56.25, 112.5, 225, 450, 900, 1800, 3600 nM; flow rate is 15 µL/min; association time is 350 seconds; dissociation time is 900 seconds; Anti-CD3e represents anti-CD3ε nanobody; Muromonab-CD3 is an immunosuppressant drug given to reduce acute rejection in patients with organ transplants, and it is a monoclonal antibody targeted at the CD3 receptor, a membrane protein on the surface of T cells.

The SPR binding assay result of the Nb-TriTE is shown in FIGS. 2A-2C, wherein FIG. 2A shows SPR kinetics assay of PD-L1 binding to Nb-TriTE, wherein the ligand is PD-L1; analyte concentrations are 100, 50, 25, 12.5, 6.25, 3.125, 1.5625, 0.78125 nM; flow rate is 30 µL/min; association time is 120 seconds; dissociation time is 900 seconds; Atezolizumab is a monoclonal antibody medication used to treat urothelial carcinoma, non-small cell lung cancer (NSCLC), triple-negative breast cancer (TNBC), small cell lung cancer (SCLC), and hepatocellular carcinoma (HCC), and it is a fully humanized, engineered monoclonal antibody of IgG1 isotype against the protein programmed cell death-ligand 1 (PD-L1); Anti-PDL1 represents anti-PD-L1 nanobody. FIG. 2B shows SPR kinetics assay of HLA-G binding to Nb-TriTE, wherein the ligand is HLA-G; analyte concentrations are 305, 152.5, 76.25, 38.125, 19.0625 nM; flow rate is 30 µL/min; association time is 180 seconds; dissociation time is 360 seconds; Anti-HLA-G represents anti-HLA-G nanobody; Anti-CD3e represents anti-CD3ε nanobody; 87G represents commercial anti-HLA-G monoclonal antibody. FIG. 2C shows SPR kinetics assay of CD3ε binding to Nb-TriTE, wherein the ligand is CD3ε; analyte concentrations are 28.125, 56.25, 112.5, 225, 450, 900, 1800, 3600 nM; flow rate is 15 µL/min; association time is 350 seconds; dissociation time is 900 seconds; Anti-CD3e represents anti-CD3ε nanobody; Muromonab-CD3 is an immunosuppressant drug given to reduce acute rejection in patients with organ transplants, and it is a monoclonal antibody targeted at the CD3 receptor, a membrane protein on the surface of T cells. As shown in FIGS. 2A-2C, the Nb-TriTE effectively binds to PD-L1, HLA-G, and CD3ε protein within the $K_D$ as 2.6, 53.3 and 3.47 nM, respectively.

Example 3

Result of T Cell Proliferation Assay of Nb-TriTE

In this example, the procedures of T cell (i.e., peripheral blood mononuclear cell (PBMC)) proliferation assay of the Nb-TriTE are as follows. $1 \times 10^5$ of PBMC cells were plating on 12-well plate. Clinical CD3ε monoclonal antibody OKT3 (5 µg, Invitrogen, Cat:MA1-10175) and Proleukin (IL-2: 200U), or 10 µg/ml of Nb-TriTE was added. After 5 or 7 days, the total cell numbers were recorded, then stained with FITC-conjugated CD3 monoclonal antibody (OKT3, 11-0037-42, eBioscience) and then analyzed by flow cytometry. The CD3 positive cells were calculated as % of CD3 cells×total cell number, and positive control was Proleukin (IL-2: 200U) and OKT3 (5 µg).

Figure 3:
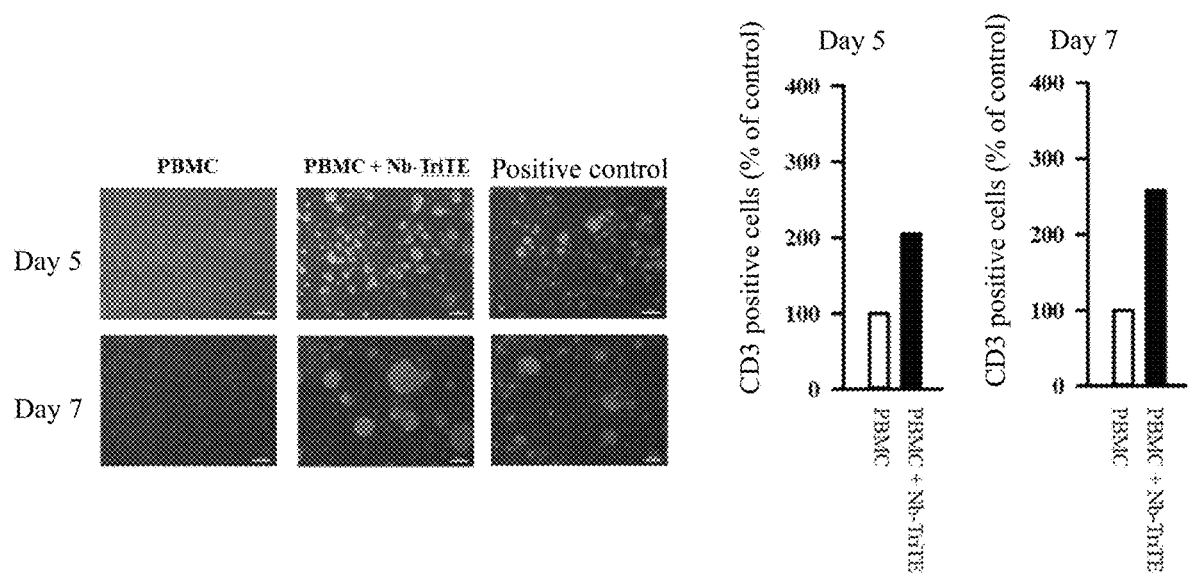
FIG. 3 shows the effect of Nb-TriTE on T cell proliferation, wherein PBMC represents peripheral blood mononuclear cell.

The effect of Nb-TriTE on T cell proliferation is shown in FIG. 3, wherein PBMC represents peripheral blood mononuclear cell. As shown in FIG. 3, the Nb-TriTE can promote T cell proliferation and activation.

Example 4

Immunocytochemistry (ICC) Staining Result of Nb-TriTE

In this example, the procedures of immunocytochemistry (ICC) for tumor cells, T cells, and Nb-TriTE (i.e., $V_HH$ nanobodies) are as follows. Tumor cells ($4 \times 10^4$ or $1 \times 10^5$) were seeded on coverslips in a 6-well plate, incubated overnight. After the indicated treatments, cells were incubated with CellTracker Green followed by adding Nb-TriTE and PBMC for one hour. Cells were then fixed in 1% paraformaldehyde, washed with PBS, permeabilized using 0.1% Triton X-100 in PBS containing 0.5% BSA for 30 min, blocked with 2% BSA, and incubated with specific antibodies in 2% BSA/PBS containing 0.05% Tween-20 (PBST). After washing, the cells were incubated with fluorescein-conjugated antibodies, washed with PBST, and mounted using a water-based mounting medium containing an anti-fade agent and 4',6-diamidino-2-phenylindole (DAPI). Images were analyzed under a Leica TCS SP8 X confocal microscope (Leica).

Figure 4:
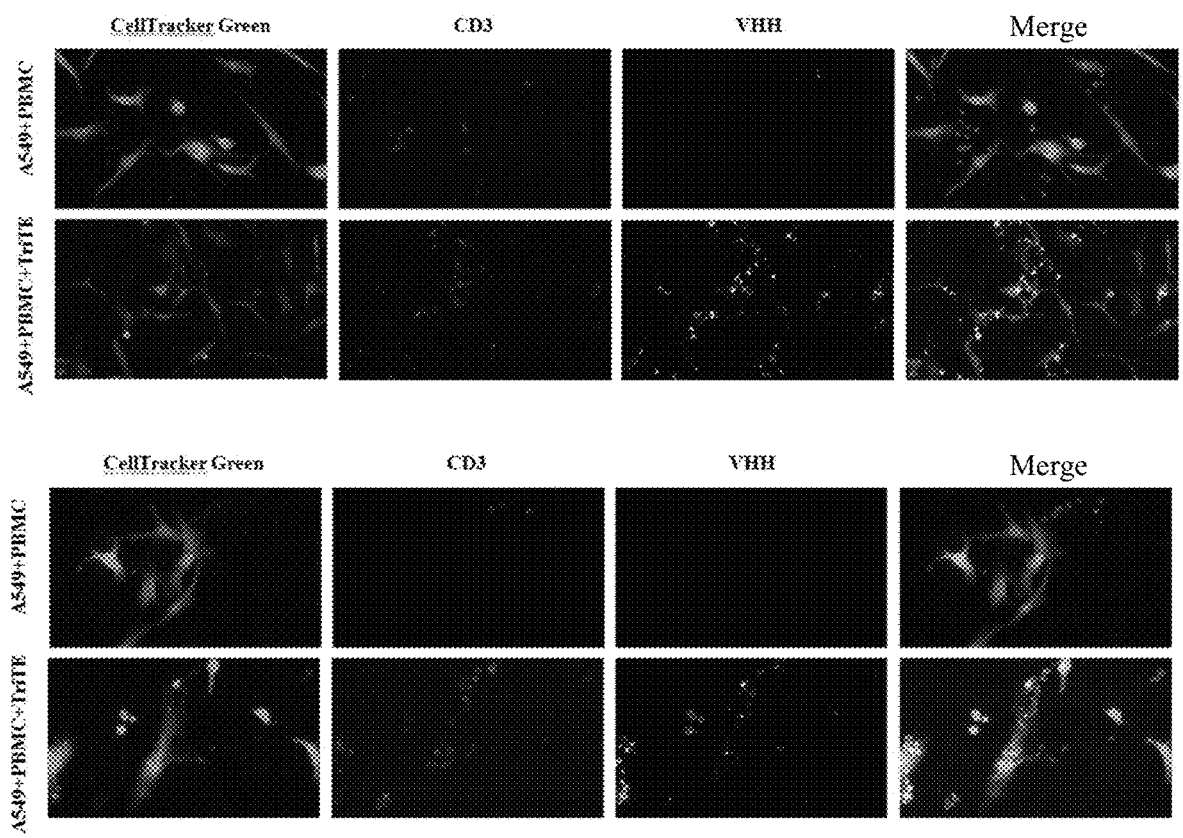
FIG. 4 shows immunocytochemistry (ICC) staining result for tumor cells, T cells, and Nb-TriTE (i.e., $V_HH$ nanobodies), wherein the A549 cell line used is human non-small cell lung cancer cell line; PBMC represents peripheral blood mononuclear cell; VHH represents Nb-TriTE; the cell number in upper figure is $1 \times 10^5$/well; the cell number in lower figure is $4 \times 10^4$/well.

The immunocytochemistry staining result for tumor cells, T cells, and Nb-TriTE (i.e., $V_HH$ nanobodies) is shown in FIG. 4, wherein the A549 cell line used is human non-small cell lung cancer cell line; PBMC represents peripheral blood mononuclear cell; VHH represents Nb-TriTE; the cell number in upper figure is $1 \times 10^5$/well; the cell number in lower figure is $4 \times 10^4$/well. The result in this example shows that the Nb-TriTE has binding ability to A549 cells.

Example 5

Evaluation of Effect of Nb-TriTE on Enhancing Cytolysis of Human Cancer Cell Lines with PBMC In this example, effect of Nb-TriTE on enhancing cytolysis of A549-human lung adenocarcinoma cell line; MDA-MB-231 (231)-human breast cancer cell line; U87-glioblastoma cell line; SKOV3-human ovarian carcinoma cell line; and FaDu-human oral cancer cell line (purchased from American Type Culture Collection, ATCC) with PBMC are evaluated. The procedure is as follows: $1 \times 10^5$ of tumor cells were plating on 12-well plate overnight. Next day, the $5 \times 10^5$ of primary PBMC were added into the wells containing tumor cells. Nb-TriTE were added. After 48 hrs, the specific lysis to tumor cells by primary PBMC were determined by LIVE/DEAD cell-mediated cytotoxicity assay using flow cytometry analysis.

Figure 5A:
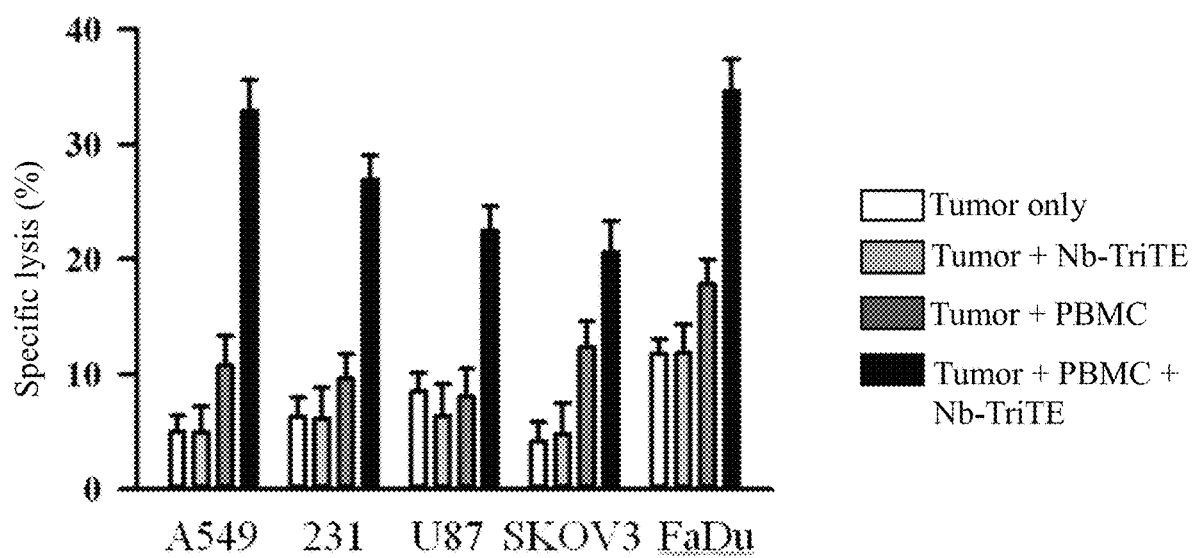
FIG. 5A shows effect of Nb-TriTE on enhancing cytolysis of human cancer cell lines with PBMC, wherein A549 represents human lung adenocarcinoma cell line; 231 represents MDA-MB-231-human breast cancer cell line; U87 represents glioblastoma cell line; SKOV3 represents human ovarian carcinoma cell line; FaDu represents human oral cancer cell line; PBMC:A549=3:1; concentration of Nb-TriTE is 10 µg/ml; co-culture for 48 hours.
Figure 5B:
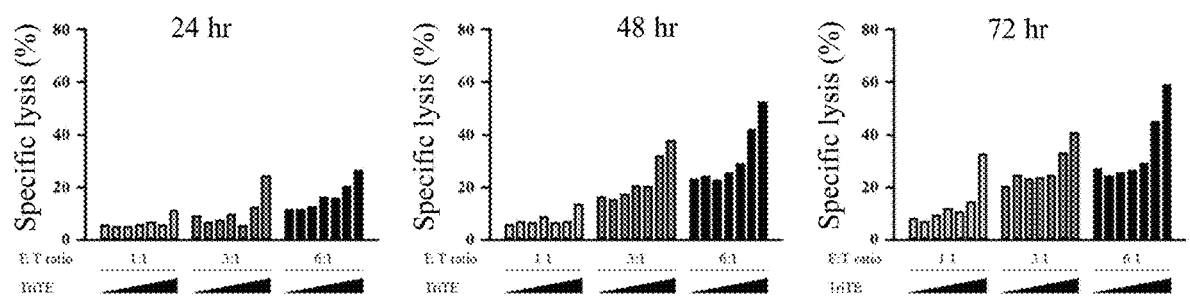
FIG. 5B shows effect of Nb-TriTE on enhancing cytolysis of human lung adenocarcinoma cell line A549 with PBMC, wherein Nb-TriTE concentrations are 0, 1, 10, 100, 1000, 10000, and 100000 µg/ml; effector (E): PBMC; target (T): A549 cell; E:T ratio represents ratio of effector/target.

The result of Nb-TriTE on enhancing cytolysis of human cancer cell lines with PBMC is shown in FIGS. 5A and 5B, wherein A549 in FIG. 5A represents human lung adenocarcinoma cell line; 231 represents MDA-MB-231-human breast cancer cell line; U87 represents glioblastoma cell line; SKOV3 represents human ovarian carcinoma cell line; FaDu represents human oral cancer cell line; PBMC:A549=3:1; concentration of Nb-TriTE is 10 µg/ml; co-culture for 48 hours; Nb-TriTE concentrations in FIG. 5B are 0, 1, 10, 100, 1000, 10000, and 100000 g/ml; effector (E): PBMC; target (T): A549 cell; E:T ratio represents ratio of effector/target. The result of this example demonstrates that Nb-TriTE enhances PBMC-induced cytotoxicity to tumor cells.

Example 6

Evaluation of Effect of Nb-TriTE on Cytokine Secretion in Co-Culture System which were Determined by Enzyme Linked Immunosorbent Assay (ELISA)

In this example, human cytokine perforin, granzyme B, tumor necrosis factor alpha (TNF-α), and interferon gamma (IFN-γ) were measured using commercial ELISA kits (Thermo Fisher Scientific). The procedure is as follows. Samples from Nb-TriTE, A549 cells, and PBMC were collected and loaded on 96-well plate overnight at 4° C. Next day, the samples were discarded, and blocked with 3% skin milk for 2 hrs at room temperature, followed by washing 5 times with PBST (0.05% Tween in PBS). After 5 times of washing, biotinylated antibodies were added for 2 hrs at room temperature. After 5 times of washing, each well was incubated with 100 µl PBST containing streptavidin-HRP conjugates for 2 hrs at room temperature. After 7 times of washing with PBST, 50 µl of TMB substrate for detecting HRP activity was added. The reactions were stopped by adding 50 µl stop solution, and it was measured by ELISA reader using 450 nm channel.

Figure 6:
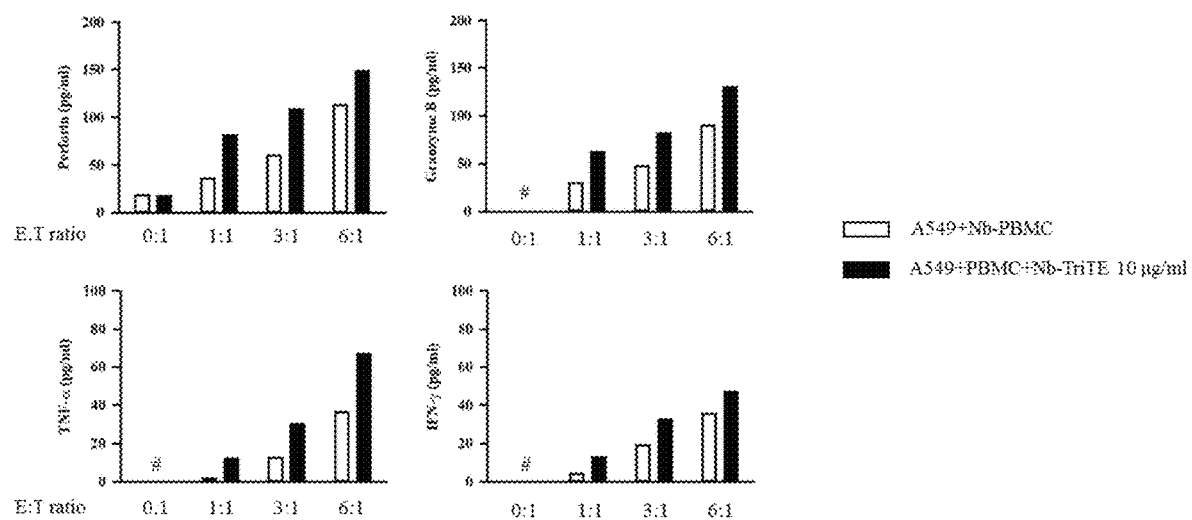
FIG. 6 shows that Nb-TriTE enhances cytokine secretion from A549 co-culture with PBMC, wherein A549 represents human lung adenocarcinoma cell line; Nb represents nanobody; effector (E): PBMC; target (T): A549 cell; E:T ratio represents ratio of effector/target; #: not detectable; TNF-α represents tumor necrosis factor alpha; IFN-γ represents interferon gamma; co-culture for 48 hours.

The result of this example is shown in FIG. 6, wherein A549 represents human lung adenocarcinoma cell line; Nb represents nanobody; effector (E): PBMC; target (T): A549 cell; E:T ratio represents ratio of effector/target; #: not detectable; TNF-α represents tumor necrosis factor alpha; IFN-γ represents interferon gamma; co-culture for 48 hours. The result of this example shows that the Nb-TriTE enhances cytokine secretion from A549 co-culture with PBMC.

Example 7

Evaluation of Effect of Nb-TriTE on Blocking Lung Cancer Growth in Humanized Mouse The procedures of this example are as follows. Six to 8 weeks old NOD/SCID gamma (NSG) mice were purchased from The Jackson Laboratory. Mice were used for the xenograft lung tumor model. For lung tumors, Luc$^+$ A549 cells were resuspended in PBS containing Matrigel, then the cells ($5\times10^5$/20 µL) were injected subcutaneously into the right back of mice. Seven days after implantation, each mouse was infused with thawed PDL1×HLA-G×CD3 Nano-TriTE and PBMC ($5\times10^6$/100 µL PBS) via tail vein injection, followed by weekly infusions of PDL1×HLA-G×CD3 Nano-TriTE. Tumor growth was monitored weekly via bioluminescence imaging using the in vivo imaging system (IVIS) (PerkinElmer). On the indicated days, mice were euthanized, and the tumors were harvested, measured, and photographed.

Figure 7A:
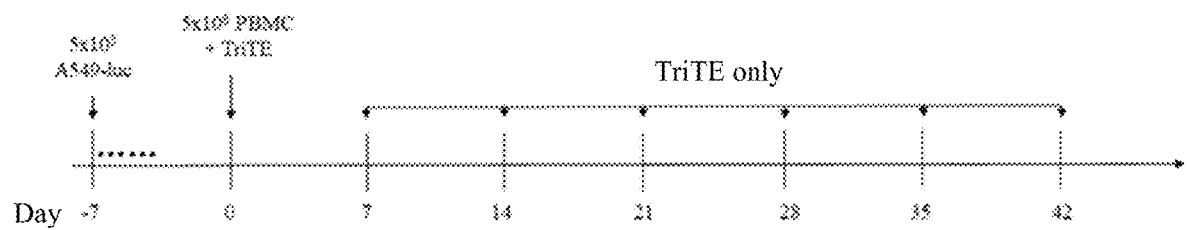
FIGS. 7A to 7C show that Nb-TriTE blocks lung cancer growth in humanized mouse model, wherein Luc in FIG. 7A represents luciferase.
Figure 7B:
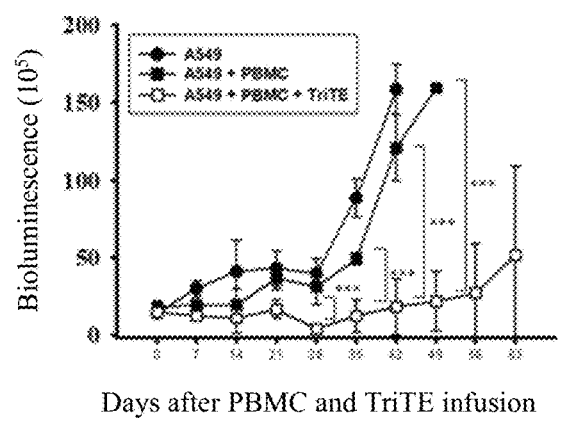
Figure 7B:
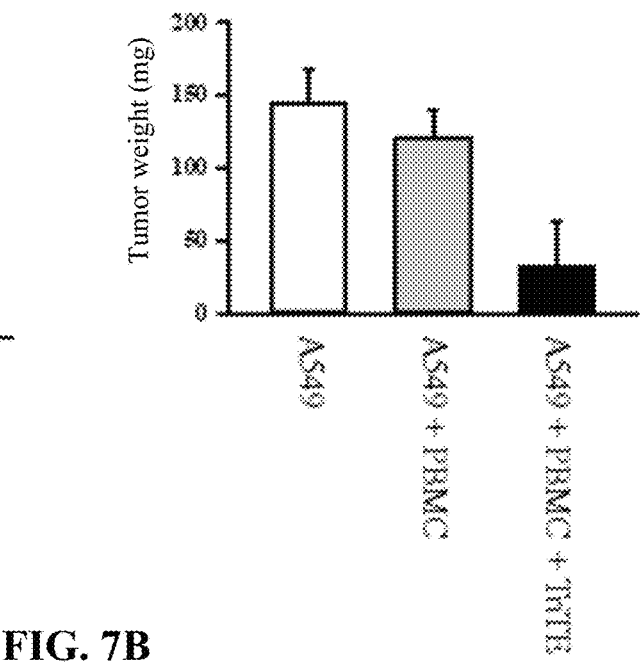
Figure 7C:
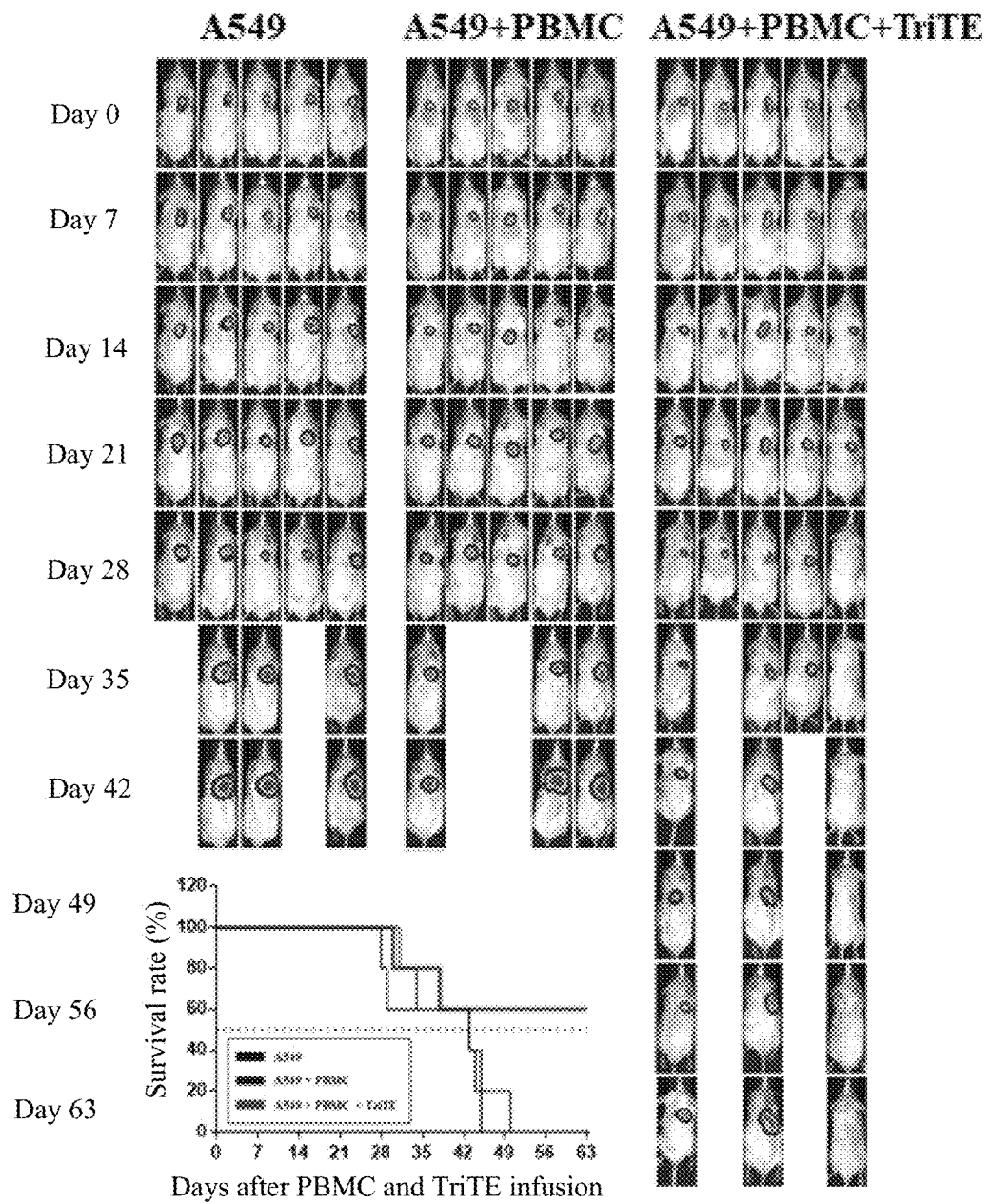

The result of this example is shown in FIGS. 7A-7C, wherein Luc in FIG. 7A represents luciferase; FIG. 7B shows the result regarding bioluminescence and tumor weight for Nb-TriTE; FIG. 7C shows the result regarding survival rate after PBMC and Nb-TriTE infusion; PBMC represents peripheral blood mononuclear cell; A549 represents human lung adenocarcinoma cell line; TriTE represents Nb-TriTE. The result of this example shows that Nb-TriTE blocks lung cancer growth in humanized mouse model.

In summary, the immunomodulation and anti-tumor-related nanobody of the present invention effectively binds to HLA-G, PD-L1 and CD3 ε, respectively, by surface plasmon resonance binding assay (SPR binding assay), promotes T cell proliferation and activation by T cell (i.e., peripheral blood mononuclear cell (PBMC)) proliferation and activation assay, enhances CD3 positive T cell proliferation in PBMCs, binds to tumor cells and kills tumor cells by immunocytochemistry (ICC) staining, enhances cytokine secretion in tumor cells by enzyme linked immunosorbent assay (ELISA), inhibits cancer cell growth by animal experiments, thereby achieving the effect of treating cancer and immune-related disorders. In particular, compared with the conventional antibodies, which have the disadvantages of low yield and poor effect, the gene must be transfected into cells by a vector to express the antibody function, the immunomodulation and anti-tumor-related nanobody of the present invention can be prepared in vitro on a large scale, and directly administered to the individual in need for treatment.

Although the present invention has been described with reference to the preferred embodiments, it will be apparent to those skilled in the art that a variety of modifications and changes in form and detail may be made without departing from the scope of the present invention defined by the appended claims.

What is claimed is:

1. An immunomodulation and anti-tumor-related nanobody that specifically binds to a human leukocyte antigen-G (HLA-G), programmed cell death ligand 1 (PD-L1) and CD3 ε (CD3 epsilon) consisting of the amino acid sequence of SEQ ID NO:1, SEQ ID NO:2, and SEQ ID NO:3, wherein the amino acid sequence of SEQ ID NO:1 is a heavy chain variable domain 2 (VHH2) of the immunomodulation and anti-tumor-related nanobody, the amino acid sequence of SEQ ID NO:2 is a heavy chain variable domain 1 (VHH1) of the immunomodulation and anti-tumor-related nanobody, and the amino acid sequence of SEQ ID NO:3 is a heavy chain variable domain 3 (VHH3) of the immunomodulation and anti-tumor-related nanobody; wherein the immunomodulation and anti-tumor-related nanobody is separated and purified by gel filtration chromatography.

2. The immunomodulation and anti-tumor-related nanobody according to claim 1, which activates and/or aggregates CD3-positive cells.

3. The immunomodulation and anti-tumor-related nanobody according to claim 2, which has effect on killing tumor cells.

4. The immunomodulation and anti-tumor-related nanobody according to claim 3, wherein the tumor cells are selected from the group consisting of: lung adenocarcinoma cells, breast cancer cells, glioblastoma cells, ovarian carcinoma cells, oral cancer cells, and a combination thereof.

5. An isolated nucleic acid encoding the immunomodulation and anti-tumor-related nanobody according to claim 1, wherein the isolated nucleic acid comprises the nucleotide sequence of SEQ ID NO:4, SEQ ID NO:5, and SEQ ID NO:6.

6. The isolated nucleic acid according to claim 5, wherein the immunomodulation and anti-tumor-related nanobody activates and/or aggregates CD3-positive cells.

7. The isolated nucleic acid according to claim 6, wherein the immunomodulation and anti-tumor-related nanobody has effect on killing tumor cells.

8. The isolated nucleic acid according to claim 7, wherein the tumor cells are selected from the group consisting of: lung adenocarcinoma cells, breast cancer cells, glioblastoma cells, ovarian carcinoma cells, oral cancer cells, and a combination thereof.

9. A pharmaceutical composition, comprising the immunomodulation and anti-tumor-related nanobody according to claim 1 and a pharmaceutically acceptable carrier.

10. The pharmaceutical composition according to claim 9, wherein the immunomodulation and anti-tumor-related nanobody activates and/or aggregates CD3-positive cells.

11. The pharmaceutical composition according to claim 10, wherein the immunomodulation and anti-tumor-related nanobody has effect on killing tumor cells.

12. The pharmaceutical composition according to claim 11, wherein the tumor cells are selected from the group consisting of: lung adenocarcinoma cells, breast cancer cells, glioblastoma cells, ovarian carcinoma cells, oral cancer cells, and a combination thereof.

13. A method for treating cancer, comprising administering to a subject in need thereof the pharmaceutical composition according to claim 9, wherein the cancer is selected from the group consisting of: lung adenocarcinoma, breast cancer, glioblastoma, ovarian carcinoma, oral cancer, and a combination thereof.

* * * * *